United States Patent [19]

Wirth et al.

[11] 3,931,262

[45] Jan. 6, 1976

[54] HYDROPHILIC AND DIFFICULTLY VOLATILE BIOCIDAL TRIORGANOTIN COMPOUNDS

[75] Inventors: Hermann Otto Wirth; Hans Joachim Lorenz, both of Bensheim-Auerbach; Hans-Helmut Friedrich, Lindenfels, Odenwald, all of Germany

[73] Assignee: Ciba-Geigy Corporation, Ardsley, N.Y.

[22] Filed: July 31, 1974

[21] Appl. No.: 493,305

Related U.S. Application Data

[63] Continuation-in-part of Ser. No. 382,633, July 25, 1973.

[30] Foreign Application Priority Data

Aug. 4, 1972  Germany............................ 2238360
July 6, 1973  Germany............................ 2334383

[52] U.S. Cl. ............. 260/429.7; 71/97; 106/308 Q; 260/45.75 K; 260/999

[51] Int. Cl.$^2$......................................... C07F 7/22

[58] Field of Search................................. 260/429.7

[56]  References Cited
UNITED STATES PATENTS

| | | | |
|---|---|---|---|
| 2,641,596 | 6/1953 | Leistner et al................... | 260/429.7 |
| 2,704,756 | 3/1955 | Leistner et al................... | 260/429.7 |
| 2,997,496 | 8/1961 | Dorfelt et al. .................. | 260/429.7 |
| 3,015,644 | 1/1962 | Leistner et al................... | 260/429.7 |
| 3,095,434 | 6/1963 | Stamm et al..................... | 260/429.7 |
| 3,129,236 | 4/1964 | Weissenberger................. | 260/429.7 |
| 3,242,201 | 3/1966 | Cramer et al.................... | 260/429.7 |
| 3,525,760 | 8/1970 | Seki et al........................ | 260/429.7 |
| 3,793,356 | 2/1974 | Williams......................... | 260/429.7 |
| 3,798,249 | 3/1974 | Overmars et al. .............. | 260/429.7 |

OTHER PUBLICATIONS

Chem. Reviews, Vol. 60, pp. 495–498 (1960).

*Primary Examiner*—Helen M. S. Sneed
*Attorney, Agent, or Firm*—Luther A. R. Hall

[57]  ABSTRACT

New triorganotin compounds which are hydrophilic and difficultly volatile are used as biocides.

34 Claims, No Drawings

HYDROPHILIC AND DIFFICULTLY VOLATILE BIOCIDAL TRIORGANOTIN COMPOUNDS

This is a continuation-in-part of our copending application Ser. No. 382,633, filed July 25, 1973.

Triorganotin compounds are valuable biocides. However, the widely used compounds, for example bis-(tri-n-butyltin)-oxide (TBTO), are highly hydrophobic in accordance with their chemical constitution. Their low water-solubility (that of TBTO is only 20 ppm) severely limits their field of use. It is extremely difficult to manufacture aqueous disinfectant solutions with them or to add them to disperse paints. The frequently used admixture with emulsifiers, for example, in the form of the commercial product "METATIN R 5710" (based on TBTO), is a long way from being able to satisfy all the requirements of practice because these emulsions have only limited durability. A further disadvantage of the trialkyltin compounds is their volatility. This volatility is the cause, for example, of the rapid loss of effectiveness of TBTO and its derivatives in many practical applications.

All tributyltin carboxylates, sulphonates, and salts with inorganic acids (chloride, sulphate, nitrate, perchlorate etc.) undergo hydrolysis on contact with water and consequently reconversion into volatile TBTO. Even more, marked is the volatility in compounds with smaller organic radicals, especially the trimethyltin derivatives. However, these compounds are of considerable commercial interest because the biocidal activity spectrum in the triorganotin series is highly specific as to structure.

This invention therefore has for its object to develop biocidal triorganotin compounds with hydrophilic properties, which are soluble in water, or at least are readily compatible with or form stable emulsions with water, and which still continue to possess only a slight volatility. The surprising discovery has been made that it is possible to effect the hydrophilic modification and reduction of the volatility with a single structural principle. The hydrophilic solubilising groups which impart the water-solubility (compatibility) and simultaneously also lower the volatility, are bonded through the mercapto-sulphur to the triorganotin radicals. Only this bond ensures a hydrolysis-resistant fixing of the solubilising groups mentioned.

A number of triorganotin mercaptides with biocidal activity have already been proposed. For example, tributyltin-2-diethylaminoethyl mercaptide

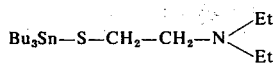

is claimed as fungicide in French Pat. No. 1.533.524.

Through the diethylamino group this compound does have a slight hydrophily, but for practical purposes this is far from being sufficient. An even more serious disadvantage is its volatility. These disadvantages only disappear if this compound — as shown in this invention — is converted into an ammonium salt.

The same applies to the tributyltin-mercapto-pyridine described in Belgian patent 707.519.

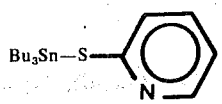

Here too only the salt formation leads to a product with hydrophilic properties which are useful for practical purposes.

Tributyltin-β-hydroxyethyl mercaptide

is cited in U.S. Pat. No. 3,382,264. This compound contains a free hydroxy group. But this is still not sufficient for the hydrophilic solubilising of the tributyltin group necessary for practical purposes. A satisfactory hydrophily is obtained only with two or more free hydroxyl groups, e.g. in the form of the monomercaptoglyceride.

Japanese Pat. No. 1977/67 claims organotin sulphaminates with a certain water-solubility. However, verification has shown that, for example, the tributyltin sulphaminate is hydrolytically split off in water at once and passes over into TBTO. As further investigations have shown, only the mercapto compound (apart from the carbon bond) is able to prevent this hydrolysis.

The invention therefore provides hydrophilic, difficultly volatile biocidal compounds of the formula I

wherein $R_1$, $R_2$, and $R_3$ each independently represents a linear or branched aliphatic group with 1 to 16 carbon atoms which can be saturated or singly olefinically unsaturated, the cyclopentyl, cyclohexyl, or phenyl group, the sum of the carbon atoms of the substituents $R_1$, $R_2$, and $R_3$ being altogether at most 18, and A represents a strongly hydrophilic group with polyether, carboxylate, sulphonate, carboxylic acid ester, carboxylic acid amide, and/or ammonium salt function.

The application also provides a process for the manufacture of compounds of the general formula I, wherein a triorganotin compound of the general formula II

in which $R_1$, $R_2$, and $R_3$ have the same meaning as in formula I and X represents OH, O½, chlorine, bromine, iodine, or acetate, is condensed in known manner with a mercapto compound of the general formula III

in which A has the same meaning as in formula I, optionally in the presence of a basic compound, accompanied by the elimination of HX.

As triorganotin compounds of the formula II there are used especially triorganotin hydroxides or triorganotin oxides.

The symbol $R_1$, $R_2$, and $R_3$ in formula I preferably represents a linear or branched alkyl or alkenyl group with 1 to 4 carbon atoms, the cyclohexyl- or the phenyl group.

Preferably two or all three of the groups $R_1$, $R_2$, and $R_3$ are the same. If two alkyl groups are the same, these are preferably methyl groups.

Exemplary of $R_1$, $R_2$, and $R_3$ in the general formula I are n-amyl, 2-methylbutyl, 3-methylbutyl, neopentyl, pentenyl-3, pentenyl-4, 3-methyl-butenyl-3, hexyl, octyl, decyl, dodecyl, tetradecyl, hexadecyl, cyclopentyl, but preferably methyl, ethyl, vinyl, n-propyl, i-propyl, n-butyl, i-butyl, butenyl-3, cyclohexyl, or phenyl.

Preferred triorganotin groups are: tri-n-butyltin, triphenyltin, tricyclohexyltin, octyl-dimethyltin, cyclohexyl-dimethyltin and phenyl-dimethyltin.

A represents in detail:

1. The radical of a polyethylene oxide with 2 to 15, preferably 8 to 11, ethylene oxide units.
2. A hydrocarbon radical with carboxylate or sulphonate function, of the formula

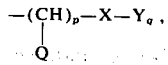

wherein Q represents hydrogen or the hydroxyl group, p is a whole number from 1 to 6, X represents $-CO_2-$ or $-SO_3-$, Y represents a counterion which is positively charged once or twice, with $q = 1$ in the first case and $a = ½$ in the second. Y is preferably sodium or the ammonium group
$NH(CH_2-CH_2-OH)_3$ Where p is O, the group X can also be

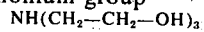

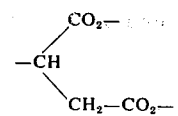

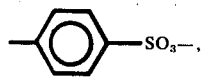

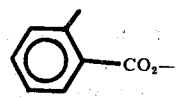

3. A hydrocarbon radical with carboxylic acid amide or, in particular, carboxylic acid ester, function, of the formula

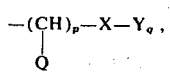

Wherein Q and p have the meanings given hereinbefore, Q is preferably hydrogen and p is preferably 1 or 2, X is $-CO-$ and $q$ is 1. Y is preferably a polyethylene oxide radical of the formula
$-O-(CH_2-CH_2-O)_n-H$
in which $n$ is 2 to 15, especially 8 to 11, a polyhydroxyalkyl radical of the formula

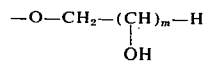

in which m is 2 to 6, or the polyhydroxyalkyl/radicals which derive from pentaerythritol, dipentaerythritol, and trismethylolpropane

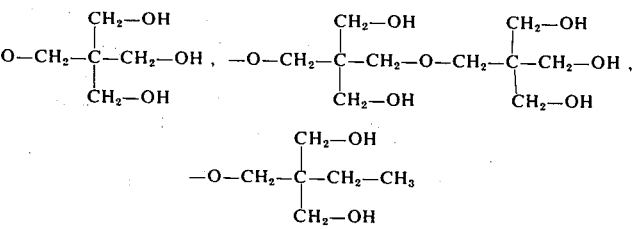

Y is also the radical of primary or secondary amine-polyethylene oxide adducts of the formula

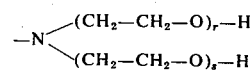

wherein $r$ and $s$ are numbers which are the same or different. The sum of $r + s$ is 2 to 15, preferably 2.

The values for $m$, $n$, $r$, and $s$ in the radicals cited hereinbefore can also be rational numbers for mean values of the chain length of the given radicals.

4. A hydrocarbon radical with an ammonium salt function, of the formula

wherein Q and p have the meanings given hereinbefore and p is preferably 2, X in its turn corresponds to the formula
$-N^+Z_3$,
and Z represents lower alkyl groups which are the same or different, polyethylene oxide radicals with 2 to 6 ethylene oxide units, and/or hydrogen, but preferably β-hydroxyethyl.

The group X can also be

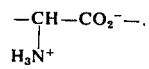

where p is O, X represents

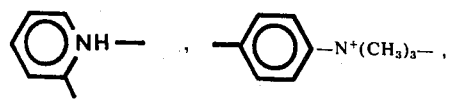

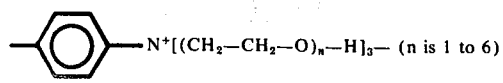

and Y represents a monovalent or divalent negative counterion, wherein in the first case $q = 1$ and in the second $q = ½$.

In the formula I -S-A preferably represents the radical of a salt of an aliphatic mercaptocarboxylic acid with at most 8, but above all at most 5, carbon atoms, and, in particular, represents the 2-mercaptopropionate or mercaptoacetate radical, wherein sodium, potassium or the triethanolamine group is preferred as cation, and very preferably -S-A is the radical of the triethanolamine salt of thioglycolic acid. In addition -S-A is preferably the radical of an ester of an aliphatic mercaptocarboxylic acid with up to 8, especially up to 5, carbon atoms, in particular of 2-mercaptopropionic acid, and polyethylene oxides with 2 to 15 ethylene oxide units, and is furthermore preferably the radical of the salt of a mercaptoalkanesulphonic acid with at most 6 carbon atoms, in particular the 3-mercaptopropionsulphonate radical.

Examples of the group A are
ad. 1. Polyethylene oxide radicals
—(CH$_2$—CH$_2$—O)$_n$—H
($n$ is 2 to 15, preferably 8 to 10) Examples of the group

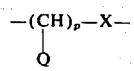

are
ad 2. Carboxylate or sulphonate radicals

—CH$_2$—CO$_2$— , —(CH$_2$)$_2$—CO$_2$— , —CH$_2$—CH—CO$_2$— ,
                                                                              OH

—(CH$_2$)$_6$—CO$_2$— , —CH$_2$—SO$_3$— , —CH$_2$—CH—SO$_3$—
                                                           OH

—(CH$_2$)$_2$—SO$_3$— , —(CH$_2$)$_5$—SO$_3$— ad 3. Carboxylic acid ester or carboxylic acid amide radicals

—CH$_2$—CO— , —(CH$_2$)$_2$—CO— , —(CH$_2$)$_5$—CO— ,

—CH$_2$—CH—CO— , —CH$_2$—CH—CH—CO— .
         OH                     OH OH

Examples of —X— as —NZ$_3$— group are
ad 4.

—NH$_3$— , —NH (CH$_3$)$_2$— , —NH (C$_2$H$_5$)$_2$— ,
—NH (CH$_2$—CH$_2$—OH)$_2$, —NH (C$_2$H$_5$)(CH$_2$—CH$_2$—OH)— ,
—N (C$_2$H$_5$)$_3$— , —N (CH$_3$) (CH$_2$—CH$_2$—OH)$_2$— ,
—N [(CH$_2$—CH$_2$—O)$_n$—H]$_3$— ($n$ is 1 to 6)

Examples of the group —Y are ad 2. A counterion which is positively charged once or twice —Na , —K , —Li , —NH$_4$ , —NH(CH$_3$)$_3$ ,
—N(CH$_3$)$_4$ ,
—NH(CH$_2$—CH$_2$—OH)$_3$ , —N(CH$_2$—CH$_2$—OH)$_4$ ,
—NH$_2$(CH$_2$—CH$_2$—OH)$_2$ , —NH(C$_2$H$_5$)(CH$_2$—CH$_2$—OH)$_2$ ,
= Ca, = Mg, = Be, = Zn, = Mn, = Sr, = Ba,

H$_3$N—CH$_2$—CH$_2$—NH$_3$ ad 3. Polyhydroxyalkyl or polyethylene oxide radicals or the radical of amine-polyethylene oxide adducts

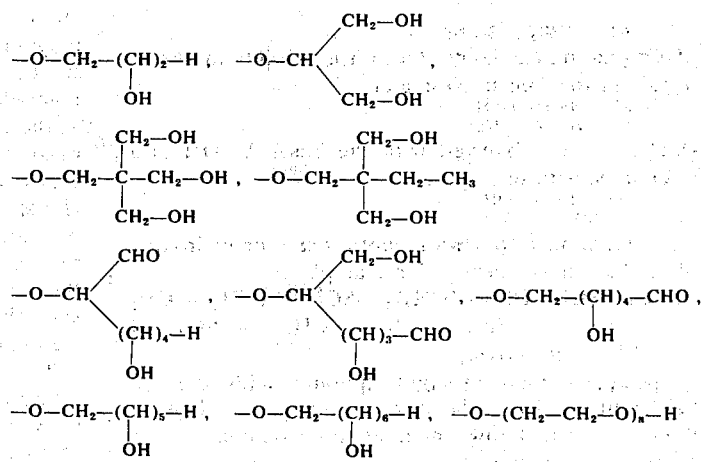

($n$ is 2 to 15, preferably 8 to 11)

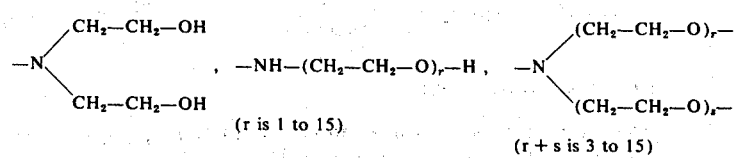
                     ($r$ is 1 to 15)            ($r + s$ is 3 to 15)

ad 4. Mono- or divalent negative counterion
—Cl, —Br, -I, —F, —NO$_3$, —BF$_4$, CH$_3$—SO$_3$—,
C$_6$H$_5$—SO$_3$— , p—CH$_3$—(C$_6$H$_4$)—SO$_3$— ,
CH$_3$—O—SO$_3$— , —ClO$_4$ , C$_2$H$_5$—O—SO$_3$— , =
SO$_4$ , = SiF$_6$ , F$_3$C—CO$_2$— , Cl$_3$C—CO$_2$—

The triorganotin-mercapto-polyethylene oxides are manufactured by reacting the free mercaptans with a tri triorganotin oxide or hydroxide, for example

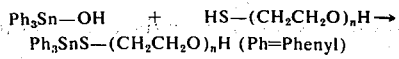
Ph₃SnS—(CH₂CH₂O)ₙH (Ph=Phenyl)

The synthesis can also be carried out starting from triorganotin halide in the presence of alkali lye, carbonate, or bicarbonate solution on the lines of a SCHOTTEN-BAUMANN reaction, e.g., Bu₃Sn—Cl + HS(CH₂CH₂O)ₙH
(Bu = Butyl)

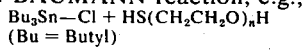

The mercapto-polyethylene oxides are obtained by the addition of polyethylene oxide to hydrogen sulphide

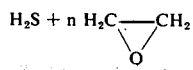

The manufacture of the triorganotin mercaptoalkylsulphonates of the formula

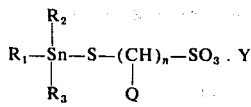

can be carried out, for example, in the following way

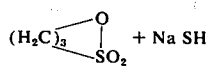

→ HS—(CH₂)₃—SO₃Na.

Using an ion exchanger (AT) it is possible to obtain therefrom the free sulphonic acid

which can be converted with the bases Y. OH into other salts, with the equation

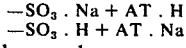

The reaction with a triorganotin oxide or hydroxide takes place subsequently, for example Ph₃Sn . OH + HS — (CH₂)₃ —SO₃ . N (CH₂ — CH₂ — OH)₄ → Ph₃Sn — S — (CH₂)₃ — SO₃ . N (CH₂—CH₂—OH)₄

The other mercaptoalkylsulphonic acids can be manufactured from the corresponding haloalkylsulphonic acids in known manner, for example via the isothiuronium halides Na . O₃S — (CH₂)ₙ —Cl + S = C (NH₂)₂

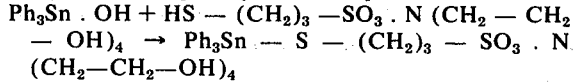

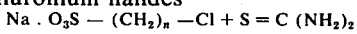

The direct reaction with, for example, potassium hydrosulphide, leads to the same result. Finally, the β-mercaptoethanesulphonic acid can also be obtained by starting from the carbyl sulphate.

The mercaptohydroxyalkylsulphonic acids can be easily obtained via the corresponding epoxides, e.g.

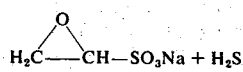

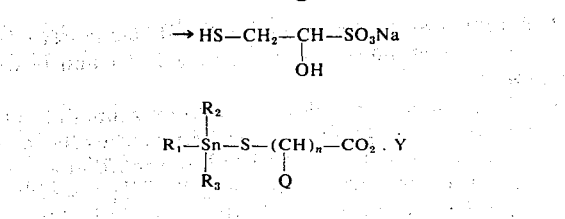

The synthesis route to the analogous triorganotin mercaptocarboxylic acid salts also proceeds via the corresponding mercaptocarboxylic acids, for which there are a number of known methods of manufacture.

The reaction (neutralisation of the carboxyl group) with the base Y is carried out advantageously after the linkage with the triorganotin group in accordance with the equation

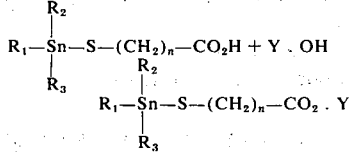

The corresponding mercapto-hydroxyalkylcarboxylic acids can also be obtained via the epoxycarboxylic acids by known methods.

Triorganotin derivatives which carry a hydrophilic carboxylic acid ester function are manufactured in two steps.

The reaction with a triorganotin oxide or hydroxide is performed after the esterification of the mercaptocarboxylic acid with a hydroxyl group of the polyol. The monoesterification with respect to a chemically unitary polyolmonoester is as a rule only possible with a substantial excess of polyol. The separation of excess (non-reacted) polyol is effected in these cases very smoothly at the end stage after the combination with the triorganotin group, on the basis of differing solubility properties, principally in chloroform or methylene chloride. However, the polyol esterification can also be carried out under stoichiometric conditions for the monoesterification. The products which are formed under these conditions do constitute statistical mixtures, but - since the monoester derivative predominates - are sufficiently hydrophilic.

If the polyol is obtainable as epoxide compound, the esterification can be effected also by the indirect route, in which case unitary polyol monoester are also formed. It is advantageous in this case to effect the linkage of the mercaptocarboxylic acid with the triorganotin group beforehand.

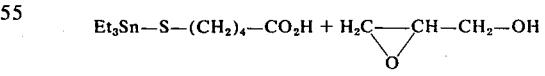

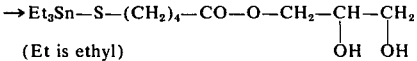
(Et is ethyl)

In obtaining the triorganotin mercaptocarboxylic acid polyethylene oxide esters, the esterification is carried out first, as with the polyol esters

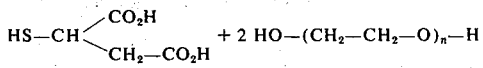

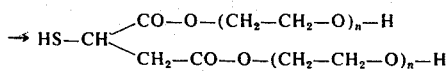

($n$ is 2 to 15)

Since these polyethylene oxides - also called polyglycols - are mostly mixtures, the triorganotin compounds resulting therefrom are not unitary products. Their commercial value is not thereby impaired.

The triorganotin mercaptocarboxylic acid amides with hydrophilic amide component can be readily manufactured from the corresponding triorganotin mercaptocarboxylic acid esters, preferably from the methyl esters, on the lines of an esteramide exchange reaction, for example

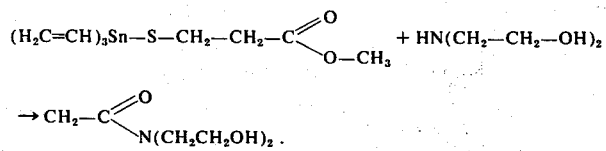

If amines which are polyethylene oxide adducts, and therefore constitute mostly mixtures, are used, then corresponding mixtures are also obtained as end product. This is not prejudical to the use of these products. Triorganotin derivatives with ammonium salt function of the formula

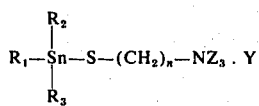

are easily manufactured. When $n$ is 2, a $\beta$-mercaptoethylamine is used as starting product

HS—CH$_2$—CH$_2$—NZ$_2$ which in its turn can be obtained by addition of the amine HNZ$_2$ to ethylene sulphide. It is possible to manufacture other mercapto amines in known manner by addition of hydrogen sulphide to amines with unsaturated ligands.

The conversion into the ammonium salt takes place advantageously after the reaction with the triorganotin compound. This is effected either with acid, preferably mineral acid, but more preferably by alkylating agents, for example, dimethyl sulphate, p-toluenesulphonic acid esters, or alkyl nitrates, e.g., i-Bu$_3$Sn—S—CH$_2$—CH$_2$—N(CH$_2$—CH$_2$—OH)$_2$ + Me$_2$SO$_4$

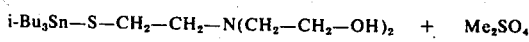
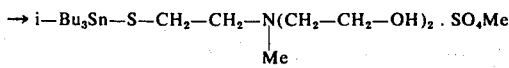

(i-Bu is isobutyl, Me is methyl)

Finally, mercapto-hydroxyalkylammonium salts can be obtained from the readily accessible epoxides, for example from glycidyltrimethylammonium chloride.

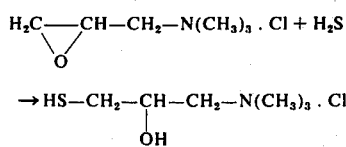

Triorganotin compounds with aromatic ligands can be readily manufactured from the known mercaptoamines, some of which are obtainable commercially. The most important reaction step for one example of a pyridinium salt is

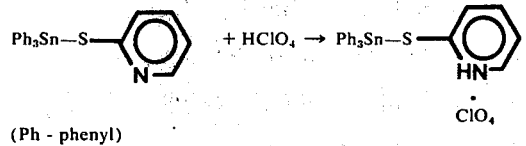

(Ph - phenyl)

Examples of compounds according to the invention are listed hereinbelow.

The following abbreviation are used: Me = methyl, Pr = propyl, Bu = butyl, Am = amyl, Hex = hexyl, Oc = octyl, Ph = phenyl.

Me$_3$Sn—S—(CH$_2$—CH$_2$—O)$_n$—H ($n\sim$4)
Ph$_3$Sn—S—(CH$_2$—CH$_2$—O)$_n$—H ($n\sim$7)
n—Pr$_3$Sn—S—(CH$_2$—CH$_2$—O)$_n$—H ($n\sim$8)
n—Bu$_3$Sn—S—(CH$_2$—CH$_2$—O)$_n$—H ($n\sim$14)

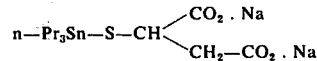

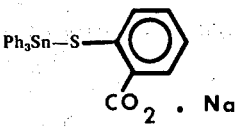

Ph$_3$Sn—S—(CH$_2$)$_6$—CO$_2$ . K
Ph$_3$Sn—S—CH$_2$—CH$_2$—CO$_2$.NH$_2$(CH$_2$—CH$_2$—CH)$_2$
n—Bu$_3$Sn—S—CH$_2$—CH$_2$—CO$_2$ . NH(CH$_2$—CH$_2$—OH)$_3$
Me$_3$Sn—S—CH$_2$—CH$_2$—CO$_2$ . NH(CH$_2$—CH$_2$—OH)$_3$

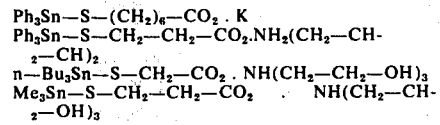

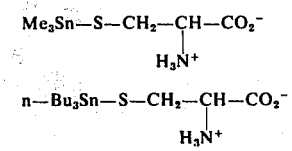

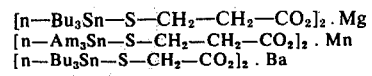

Ph$_3$Sn—S—CH$_2$—CH$_2$—SO$_3$ . N(CH$_3$)$_4$
(Me$_3$Sn—S—CH$_2$—CH$_2$—SO$_3$)$_2$ . Ca
(Ph$_3$Sn—S—CH$_2$—CH$_2$—CH$_2$—SO$_3$)$_2$ . Mg
[(C$_2$H$_5$)$_3$Sn—S—CH$_2$—CH$_2$—SO$_3$]$_2$ . Zn

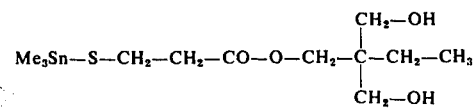

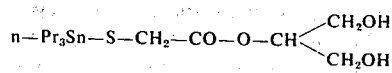
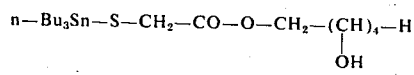
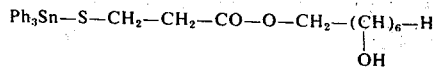
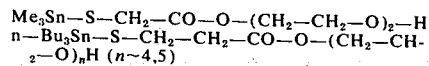
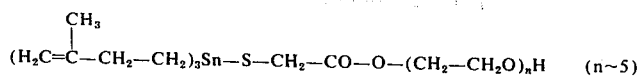
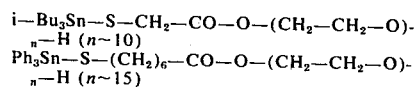
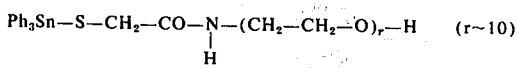
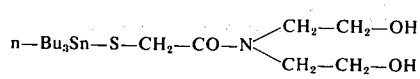
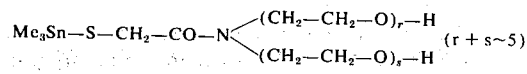
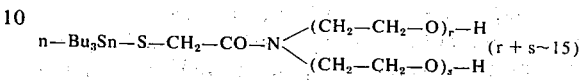
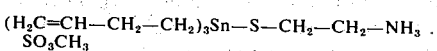
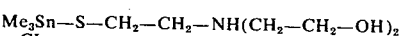
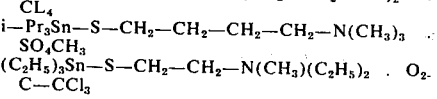
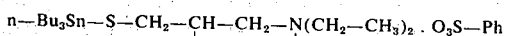
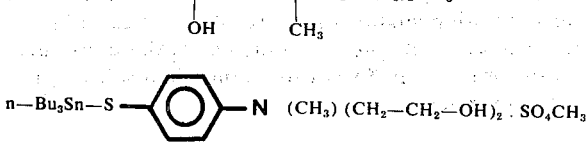
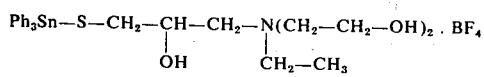
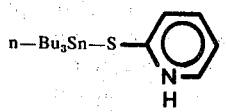
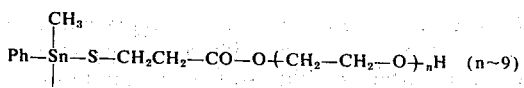
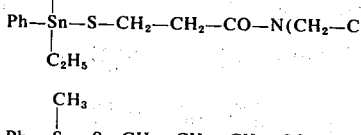
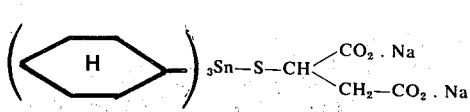
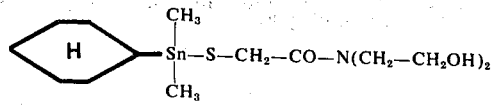
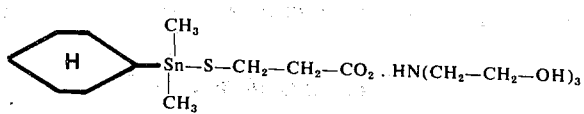

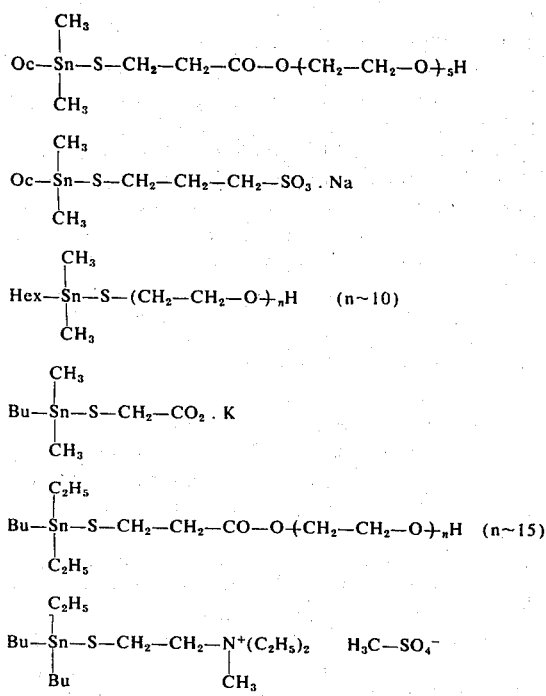

Preferred compounds are:

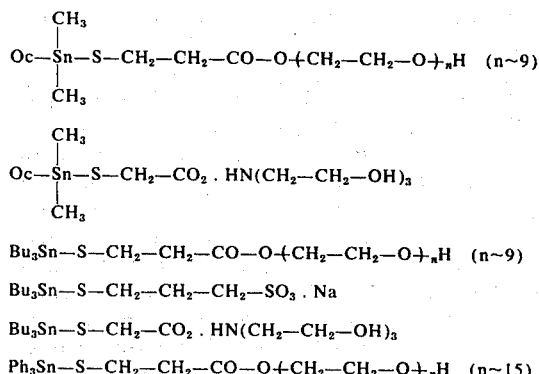

Bu₃Sn—S—CH₂—CH₂—CO—O—(CH₂—CH₂—O)ₙH   (n~9)

Bu₃Sn—S—CH₂—CH₂—CH₂—SO₃ . Na

Bu₃Sn—S—CH₂—CO₂ . HN(CH₂—CH₂—OH)₃

Ph₃Sn—S—CH₂—CH₂—CO—O—(CH₂—CH₂—O)ₙH   (n~15)

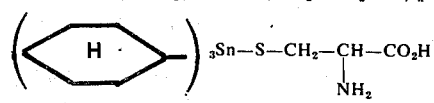

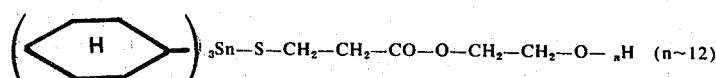

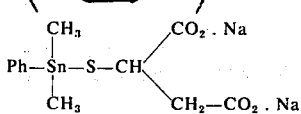

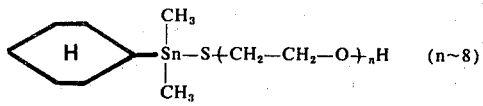

The substance of the present invention possess marked hydrophilic properties. Moreover, they simultaneously fulfill the requirement of slight volatility.

By appropriate choice of the group A it is possible to attain substantial gradations of these properties for particular applications. Thus it is possible to obtain from one and the same triorganotin group derivatives which are miscible with water to a practically unlimited extent, while others display good emulsiying properties.

TABLE 1

Solubility properties of tributyltin derivatives

General formula: (butyl)₃Sn—S—A

| A | Solubility in water |
|---|---|
| —CH₂—CH₂—N̈(—CH₂—CH₃)₂·O₃S O CH₃ with CH₃ branch | extremely good |
| —CH₂—CH₂—CH₂—SO₃ . Na | good (tenside-like behaviour) |

COMPARISON

| A | Solubility in water |
|---|---|
| —CH₂—CH—CH₂ with OH OH | satisfactory |
| bis(n-tributyl-tin)-oxide (TBTO) | poor (20 ppm) |

The solubilising effect of a particular hydrophilic group naturally depends also on the triorganotin species itself. Large organic radicals (e.g. amyl or phenyl) require for a specific water-solubility of the resulting compound stronger solubilising groups than small organic radicals (e.g. methyl).

The quaternary ammonium group produces a very strong (already extreme) solubilising effect. The triorganotin compounds provided therewith — they are almost always honey — or wax-like substances — are in most cases miscible with water in any proportion. Very marked is also the solubilising effect of the sulphonate group in the form of the alkali salts. These substances display the typical behaviour of tensides (soaps), i.e., they form mostly micellar solutions and thereby also lower the surface tension of the water. The influence of the counterion is here more marked than in the case of the ammonium salts. Coupled with the strongly hydrophilic quaternary ammonium ions - for example with the tetra-($\beta$-hydroxyethyl)-ammonium group - it is possible to obtain extremely good water-solubility.

With the corresponding carboxylates the water-solubility is reduced somewhat under otherwise comparable structural prerequisites. Substances with the typical behaviour of soaps are also available in the form of alkali salts. The aqueous solutions also display the alkaline reaction which is typical of alkali carboxylate soaps, and like these they form very stable emulsions.

Very similar are the solubility properties of the triorganotin carboxylic acid esters and amides (with hydrophilic alcohol or amin moiety). It can be said that there is a direct connection between the hydrophily and consequently of the water-solubility on the one hand, and the number of the hydroxyl groups and the length of the polyethylene oxide radicals on the other. The same applies also to the pure polyethylene oxide derivatives. All these products have a honey- or wax-like consistency.

In the compounds according to the invention the triorganotin bond is completely stable to hydrolysis in neutral medium. Only in a strongly acid or alkaline pH range does cleavage slowly commence.

The compounds of this invention are outstanding biocides. With them it is possible to manufacture aqueous disinfectant solutions which can be used with complete success in human and veterinary medicine. The disinfecting of seeds and wood conservation - also from aqueous liquor - are other fields of application for these substances. They can also be used with particular advantage as additives for pigment dye dispersions and disperse paints, both in respect of storage and of the long-lasting protective action of the coating. Furthermore these substances can be used in antifouling paints, whereby they prevent both the harmful growth of sea organisms and improve — as a result of the hydrophilic radical — the hydrodynamic properties on the ship's stern.

A further field of application for these substances is mucilage control in paper manufacture, thereby also simultaneously ensuring paper conservation.

Certain thermoplasts and elastomers, in particular PVC with plasticiser content, can be effectively protected by the substances against attack by microbes. An antistatic finish is thereby simultaneously provided.

The substances of the present invention are also valuable herbicides for various cultivated plants. In cotton growing they can be used as defoliants and desicants.

In many cases the phytotoxicity of the triorganotin compounds according to the invention is distinctly lower than of the corresponding known compounds, thereby ensuring their favourable use in plant protection. Their activity against phytopathogenic fungi in cereal disinfection extends, for example, over Fusarium nivale, Tilletia caries, Helminthosporium gramineum, Septoria nodorum. The activity against soil fungi comprises, for example, Fusarium oxysporium, Pythium debarynum, hizoctonia solani, Verticileum albo atrum. In fungoid leaf infections the following species, for example, are attached and destroyed: Botrytis cinerea, rust fungi, e.g., Cloromyces and puccinia, powdery mildews, e.g., Phytophthora and Plasmopara, Pseudoperonospera.

Total activity was obsered e.g., against the following leaf fungi: Botrytis cinerea in Vicia faba, Plasmopora viticola (Bert, et Curt,), (Berl. et de Toni) on vines; in the disinfectant test against Fusarium nivale and Tilletia caries. This statement, however, does not constitute any limitation.

In the test for microbiocidal activity the compounds listed hereinbelow yielded the values indicated in the following Table:

| No. | Compound |
|---|---|
| 1 | (n—C₄H₉)₃Sn—S—CH₂—CH₂—COO.(CH₂—CH₂—O)ₙ—H    (n~9) |
| 2 | (C₆H₅)₃Sn—S—(CH₂)₃—SO₃.Na |
| 3 | (H-phenyl with CH₃, CH₃ substituents)—Sn—S—CH₂—CH₂—COO—(CH₂—CH₂—O)ₙ.H    (n~9) |
| 4 | (n—C₄H₉)₃Sn—S—CH₂—COO.H.N(CH₂CH₂OH)₃ |

-continued

| No. | Compound |
|---|---|
| 5 | $(n-C_4H_9)_3Sn-S-(CH_2)_2-COO.H.N(CH_2CH_2OH)_3$ |
| 6 | $(n-C_4H_9)_3Sn-S-CH_2-CO.N(CH_2CH_2OH)_2$ |

Table

| Bacteria | | | Microbiological Test Activity range in ppm * | 1 | 2 | 3 | 4 | 5 | 6 |
|---|---|---|---|---|---|---|---|---|---|
| Staphylococcus | aureus | SG 511 | | 10 | 3 | 10 | 30 | 10 | 30 |
| | | SG 511 | M6 | 10 | 10 | — | 30 | 30 | 3 |
| Sarcina | ureae | SMB 81 | | 10 | 3 | 10 | 30 | 30 | 1 |
| Streptococcus | faecalis | NCTC 8619 | | 10 | 10 | 10 | 30 | 100 | 30 |
| | agalactiae | | M100 | 3 | 3 | — | 30 | 30 | 3 |
| Corynebacterium | diphteroides | FUR | | 10 | 3 | 3 | 30 | 10 | 1 |
| Bacillus | subtilis | NCTC 6460 | | 10 | 3 | 3 | 30 | 10 | 1 |
| Mycobacterium | phlei | CITM 61 | | 3 | 3 | 3 | 30 | 10 | 1 |
| Escherichia | coli | NCTC 8195 | | 10 | 30 | 10 | 30 | >300 | 30 |
| | | RP 45410 | | 10 | 10 | 10 | 30 | >300 | 30 |
| Arizona | paracolon | 7:1.7,8 | | >300 | >300 | — | >300 | >300 | >300 |
| Salmonella | pullorum VBIZ | | | >300 | >300 | 100 | >300 | >300 | >300 |
| | gallinarum | | VBIB | >300 | >300 | — | — | — | — |
| | cholerae-suis | | VBIB | >300 | >300 | 100 | >300 | >300 | >300 |
| Pasteurella | multocida | K753 | | 10 | >300 | 10 | 30 | 30 | 30 |
| Pseudomonas | fluorescens | | | 10 | >300 | 30 | >300 | 30 | 30 |
| | | NCTC 4755 | | | | | | | |
| Fungi | | | | | | | | | |
| Trichophyton | gypseum | CBS | | 30 | 30 | 10 | 10 | 10 | 10 |
| Fusarium spec. | | DAP | | 30 | 30 | — | — | — | — |
| Pilz schwarzlich | | DAP | | 10 | 30 | — | — | — | — |
| Candida albicans | | CBS | | 30 | 30 | 3 | 10 | 10 | 10 |
| Hefe | | DAP | | 10 | 10 | — | — | — | — |
| Hefe rot | | DAP | | 10 | 10 | — | — | — | — |
| Aspergillus | niger | ATCC 6275 | | 30 | 30 | 10 | 10 | 10 | 10 |
| | flavus | CBS 12662 | | 30 | 30 | 3 | 10 | 10 | 10 |
| Penicillium | funiculosum | CEB 329631 | | 30 | 100 | 10 | 30 | 10 | 30 |
| | expansum | SMC 36 | | 30 | 30 | 3 | 10 | 10 | 10 |
| Trichoderma | viride | CEB 3334.2 | | 100 | 10 | 10 | 10 | 10 | 10 |
| Fusarium | oxysporum | CBS | | 30 | 10 | 3 | 10 | 10 | 10 |
| Chaetomium | globosum | CBS 14851 | | 10 | 10 | 3 | 10 | 3 | 3 |
| Alternaria | tenuis | CBS 10426 | | 30 | 10 | 3 | 10 | 3 | 3 |
| Paecilomyces | varioti | CBS | | 30 | 10 | 3 | 10 | 3 | 3 |
| Stachybotrys | atra | CBS 32465 | | 10 | 10 | 3 | 10 | 3 | 3 |
| Pullularia | pullulans | CBS 10767 | | 10 | 3 | — | 10 | 10 | 10 |
| Coniphora | cerebella | CBS | | 10 | 30 | — | 10 | 10 | 10 |
| Poria | vaporia | CBS | | 100 | 3 | — | 10 | 10 | 10 |
| Polystictus | versicolor | EMPA61 | | 100 | 30 | — | 100 | 30 | 30 |
| Lenzites | abietina | CBS | | 10 | 100 | — | 10 | 10 | 10 |

* = virulent strains

Results of the test of growth resistance on the beer bottling plant of a brewery:

1. white pigmented disperse paint based on a finely dispersed polyvinylpropionate copolymer finished with

| (g of additive per kg of ready for brushing paint) | | free from growth |
|---|---|---|
| 2,5 | g of tributyl-tin oxide (TBTO) | 7 months |
| 10,0 | g of a TBTO preparation containing 25% TBTO | 8 " |
| 20,0 | g of Mergal 10 S (commercially obtainable mercury compound) | 8 " |
| 3,25 | g $Me_3Sn-S-(CH_2)_2.COO.CH_2.C(CH_2OH)_2.CH_2.CH_3$ | 10 " |
| 3,4 | g $Bu_3Sn-S-CH_2.COO.Na$ | 10 " |
| 3,7 | g $(C_3H_7)_3Sn-S-CH(COO.Na).CH_2.COO.Na$ | 10 " |
| 3,8 | g $(Bu_3Sn-S-CH_2.COO)_2.Ba$ | 10 " |
| 3,95 | g $Bu_3Sn-S-(CH_2)_3.SO_3.Na$ | 10 " |
| 4,25 | g $[CH_3.C(CH_3)_2.CH_2]_3Sn-S-(CH_2)_3.SO_3.NH_4$ | 10 " |
| 5,0 | g $Me_3Sn-S-(CH_2.CH_2.O)_n.H$ (n~10) | 12 " |
| 3,35 | g $Me_3Sn-S-(CH_2.CH_2.O)_n.H$ (n~4) | 13 " |
| 3,7 | g $Bu_3Sn-S-[C_5H_4N].HCl$ | 13 10 " |
| 3,95 | g $Bu_3Sn-S-CH_2.CO.N(CH_2.CH_2OH)_2$ | 13 " |
| 4,5 | g $Bu_3Sn-S-CH_2.COOH.N(CH_2.CH_2OH)_3$ | 13 " |
| 4,9 | g $Bu_3Sn-S-CH_2.COO.(CH_2.CH_2.O)_n.H$ (n~4,5) | 13 " |
| 5,0 | g $Bu_3Sn-S-CH_2.CH_2.COO.(CH_2.CH_2.O)_n.H$ (n~4,5) | 13 " |
| 5,2 | g $[CH_2=C(CH_3).CH_2.CH_2]_3Sn-S-CH_2.COO.(CH_2.CH_2.O)_n.H$ (n~5) | 13 " |
| 6,6 | g $Bu_3Sn-S-CH_2.COO.(CH_2.CH_2.O)_n.H$ (n~9) | 13 " |
| 6,7 | g $Bu_3Sn-S-CH_2.CH_2.COO.(CH_2.CH_2.O)_n.H$ (n~9) | 13 " |

-continued

| (g of additive per kg of ready for brushing paint) | | free from growth | |
|---|---|---|---|
| 7,2 | g Ph₃Sn—S—CH₂.CH₂.COO.(CH₂.CH₂.O)ₙ.H (n~9) | 13 | " |
| 7,75 | g Bu₃Sn—S—(CH₂.CH₂.O)ₙ.H (n~14) | 13 | " |

2. White pigmented disperse paint based on a finely dispersed styrene-butadiene copolymer finished with

| (g of additive per kg or ready for brushing paint) | | free from growth | |
|---|---|---|---|
| 2,5 | g tributyl-tin oxide (TBTO | 7 months | |
| 20 | g Mergal ᴿ 10 S | 7 | " |
| 4,35 | g [Ph₃Sn—S—(CH₂)₃.SO₃]₂.Mg | 9 | " |
| 4,35 | g (C₂H₅)₃Sn—S—CH₂.CH₂.N(CH₃)(CH₂.CH₃)₂.OOC.CCl₃ | 10 | " |
| 4,45 | g Ph₃Sn—S—(CH₂)₃.SO₃.Na | 10 | " |
| 4,65 | g Ph₃Sn—S—(CH₂)₆.COO.K | 10 | " |
| 4,95 | g Ph₃Sn—S—CH₂—COOH.N(CH₂.CH₂OH)₃ | 10 | " |
| 3,35 | g Me₃Sn—S—(CH₂.CH₂.O)ₙ.H (n~4) | 11 | " |
| 3,95 | g Bu₃Sn—S—CH₂.CO.N(CH₂.CH₂OH)₂ | 11 | " |
| 4,5 | g Bu₃Sn—S—CH₂.COOH.N(CH₂.CH₂OH)₃ | 11 | " |
| 4,9 | g Bu₃Sn—S—CH₂ .COO.(CH₂.CH₂.O)ₙ.H (n~4,5) | 11 | " |
| 5,0 | g Bu₃Sn—S—CH₂.CH₂.COO.(CH₂.CH₂.O)ₙ.H (n~4,5) | 11 | " |
| 5,2 | g (CH₂=C(CH₃).CH₂.CH₂)₃Sn—S—CH₂.COO.(CH₂.CH₂.O)ₙ.H (n~5) | 11 | " |
| 6,6 | g Bu₃Sn—S—CH₂.COO.(CH₂.CH₂.O)ₙ.H (n~9) | 11 | " |
| 6,7 | g Bu₃Sn—S—CH₂.COO.(CH₂.CH₂.O)ₙ.H (n~9) | 11 | " |
| 7,2 | g Ph₃Sn—S—CH₂.COO.(CH₂.CH₂.O)ₙ.H (n~9) | 11 | " |
| 7,75 | g Bu₃Sn—S—(CH₂.CH₂.O)ₙ.H (n~14) | 11 | " |
| 3,7 | g Bu₃Sn—S—[C₅H₄N].HCl | 12 | " |

The tin compounds are used in these experiments in the same molar ratio.

EXAMPLE I:

S-tri-n-butyl-tin-thioglycolic acid polyethylene glycol ester $$(C_4H_9)_3Sn-S-CH_2-COO-(CH_2-CH_2-O)_n-H$$
$$(n\sim 9)$$

80 parts of polyethylene glycol (MG~400), 18,4 parts of thioglycolic acid, and 100 parts of toluene are heated under reflux with stirring until the water of reaction is removed by circulation. Subsequently 60 parts of bis-(tri-n-butyl-tin)-oxide are added and the water of reaction is once more removed by circulation. The solvent is the distilled off under reduced pressure.
Yiel: 151 parts (99% of theory); colourless liquid;
Sn calc. 15,5%, found 15,6%

EXAMPLE II:

S-tri-n-butyl-tin-thioglycolic acid-polyethylene glycol ester

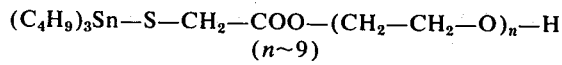
$(n\sim 4,5)$

The synthesis is carried out under the conditions described in Example I.

| Batch: | 20 | parts of polyethylene glycol (MG~200) |
|---|---|---|
| | 9.2 | parts of thioglycolic acid |
| | 30 | parts of bis-(tri-n-butyl-tin)-oxide |
| | 100 | parts of toluene |
| Yield: | 54 | parts (97,5% of theory); colourless liquid: $n_D^{20}$: 1.5012. |
| | | Sn calc. 21,4%, found 20,9%. |

EXAMPLE III:

S-tri-n-butyl-tin-β-mercaptopropionic acid polyethylene glycol ester
$$(C_4H_9)_3Sn-S-CH_2-CH_2-COO-(CH_2CH_2-O-)_n-H \ (n\sim 9)$$

The synthesis is carried out under the conditions described in Example I.

| Batch: | 80 | parts of polyethylene glycol (MG~400) |
|---|---|---|
| | 21.2 | parts of β-mercaptopropionic acid |
| | 60 | parts of bis-(tri-n-butyl-tin)-oxide |
| | 100 | parts of toluene |
| Yield: | 154 | parts (99% of theory); yellowish liquid: $n_D^{20}$: 1.4921 |
| | | Sn calc. 15,3%, found 15,2% |

EXAMPLE IV:

S-tri-butyl-tin-β-mercaptopropionic acid polyethylene glycol ester $(C_4H_9)_3Sn—S—CH_2—CH_2—COO—(CH_2—CH_2—O)_n—H$ ($n \sim 4,5$)

The synthesis is carried out under the conditions described in Example I.

| Batch: | 20 | parts of polyethylene glycol (MG~200) |
|---|---|---|
| | 10.6 | parts of β-mercaptopropionic acid |
| | 30 | parts of bis-(tri-n-butyl-tin)-oxide |
| | 100 | parts of toluene |

The reaction product was filtered over a filter aid.

| Yield: | 51 | parts (88% of theory); colourless liquid: $n_D^{20}$: 1,4990. Sn calc. 20,6%, found 20,2%. |
|---|---|---|

EXAMPLE V:

S-tri-n-butyl-tin-mercaptosuccinic acid-bispolyethylene glycol ester

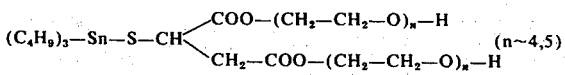
$(n \sim 4,5)$

The synthesis is carried out under the conditions described in Example I.

| Batch: | 40 parts of polyethylene glycol (MG~200) |
|---|---|
| | 15 parts of thiosuccinic acid |
| | 30 parts of bis-(tri-n-butyl-tin)-oxide |
| | 100 parts of toluene |

The reaction product was filtered over a filter aid.

| Yield: | 79 | parts (98,5% of theory); colourless liquid; $n_D^{20}$: 1.5000. Sn calc. 14,8%, found 14,7%. |
|---|---|---|

EXAMPLE VI:

S-triphenyl-tin-β-mercaptopropionic acid-polyethylene glycol ester $Ph_3Sn—S—CH_2—CH_2—COO—(CH_2—CH_2—O)_n—H$ ($n \sim 9$)

The synthesis is carried out under the conditions described in Example I.

| Batch: | 26,5 | parts of β-mercaptopropionic acid |
|---|---|---|
| | 100,0 | parts of polyethylene glycol (MG~400) |
| | 99,0 | parts of triphenyl tin hydroxide |
| | 200.0 | parts of toluene |
| Yield: | 202 | parts (97% of theory); yellow viscous liquid; $n_D^{20}$: 1.5584 Sn calc. 14,2%, found 14,5%. |

EXAMPLE VII:

1-(S-trimethyl-tin)-mercapto-polyethylene oxide
$(CH_3)_3Sn—S—(CH_2—CH_2—O)_n—H$ ($n \sim 10$)

While stirring, 47 parts of 1-mercapto-polyethylene oxide $HS—(CH_2—O)_n—H$; ($n \sim 10$), 18 parts of trimethyl tin hydroxide, and 100 parts of toluene are heated under reflux until the water of reaction has been quantitatively removed by circulation. The solvent is then distilled off under reduced pressure.

Yield: 61 parts (96% of theory); yellowish viscous liquid.
Sn calc. 19,6% found 18,4%
S calc. 5,0%, found 4,8%.

EXAMPLE VIII:

1-(S-trivinyl tin)-mercapto-polyethylene oxide
$(CH_2=CH)_3Sn—S—(CH_2—CH_2—O)_n—H$ ($n \sim 8$)

The synthesis is carried out under the conditions described in Example VII.

| Batch: | 36 | parts of 1-mercapto-polyethylene oxide ($n \sim 8$) |
|---|---|---|
| | 22 | parts of trivinyl tin hydroxide |
| | 100 | parts of toluene |
| Yield: | 54 | parts (96% of theory); yellowish viscous liquid; Sn calc. 21,2%, found 21,2% S calc. 5,7%, found 5,55%. |

EXAMPLE IX:

1-(S-tri-n-butyl tin)-mercapto-polyethylene oxide
$(C_4H_9)_3Sb—S—(CH_2—CH_2—O)_n—H$ ($n \sim 14$)

The synthesis is carried out under the conditions described in Example VII.

| Batch: | 62 | parts of 1-mercapto-polyethylene oxide ($n \sim 14$) |
|---|---|---|
| | 30 | parts of bis-(tri-n-butyl-tin)-oxide |
| | 100 | parts of toluene |
| Yield: | 90 | parts (98% of theory); yellowish viscous liquid. Sn calc. 13,1%, found 12,9% S calc. 3,5%, found 3,4%. |

EXAMPLE X:

S-tri-n-butyl tin-mercaptodiethanol
$(C_4H_9)_3Sn.S—(CH_2—CH_2—O)_2—H$

While stirring, a mixture of 60 parts of bis-(tri-n-butyl tin)-oxide, 24,4 parts of mercaptodiethanol, and 100 parts of toluene is stirred under reflux until the water of reaction is quantitatively removed by circulation. The solvent is subsequently distilled off in vacuo.
Yiel: 81 parts (99% of theory); colourless liquid: $n_D^{20}$: 1.5168.
Sn calc. 28,9%, found 28,8%.

EXAMPLES XI:

β-(S-tri-i-butyl tin)-mercaptopropionic acid-1,1,1-trismethylolpropane monoester

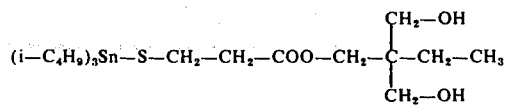

While stirring, 107,2 parts of 1,1,1-tris-(hydroxymethyl)-propane, 21,2 parts of 2-mercaptopropionic acid, and 250 parts of toluene are heated under reflux until the water of reaction has been quantitively removed by circulation. Subsequently 60 parts of bis-(tri-i-butyl tin)-oxide are added and the water of reaction is once more removed by circulation. The solvent is then distilled off under reduced pressure, and subsequently excess tris-(hydroxymethyl)-propane is distilled off in an oil pump vacuum.

Yield: 101 parts (99% of theory); honey-like consistency.
Sn calc. 23.2%, found 23,0%
S calc. 6,3%, found 6,0%

EXAMPLE XII:

sodium S-tri-n-butyl tin-thioglycolate
$(C_4H_9)_3Sn—S—CH_2—CO_2.Na$

While stirring, 29,8 parts of bis-(tri-n-butyl tin)-oxide, 10,1 parts of thioglycolic acid, and 100 parts of toluene are heated under reflux until the water of reaction has been quantitively removed by circulation. A solution of 4,4 parts of sodium hydroxide in 50 parts of methanol is subsequently added, the batch is heated under reflux for 10 minutes, and the solvent distilled off under reduced pressure.

Yield: 39,1 parts (97% of theory); wax-like substance.
Sn calc. 29,45%, found 29,2%.

EXAMPLE XIII:

calcium β-(S-tri-n-butyl tin)α-hydroxy-propionate
$[(C_4H_9)_3Sn—S—CH_2—CH(OH)—CO_2]_2Ca$ The synthesis is carried out under the conditions described in Example XII.

| Batch: | 59,6 parts of bis-(tri-n-butyl tin)-oxide |
| --- | --- |
| | 26,4 parts of 1-hydroxy-2-mercaptopropionic acid |
| | 200 parts of toluene |
| | 5,6 parts of calcium oxide |
| Yield: | 93 parts (98% of theory); whit powder; m.p. 230° – 20°C (with decomp.) |
| | Sn calc. 25.0%, found 24,8% |
| | S calc. 6,7%, found 6,5%. |

EXAMPLE XIV:

sodium S-tri-n-propyl-mercaptosuccinate

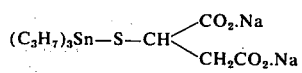

The synthesis is carried out under the conditions described in Example XII.

| Batch: | 25,6 parts of bis-(tri-n-propyl tin)-oxide |
| --- | --- |
| | 15.0 parts of thiosuccinic acid |
| | 100 parts of toluene |
| | 8.8 parts of sodium hydroxide |
| | 100 parts of methanol |
| Yield: | 44 parts (100% of theory); soap-like consistency. |
| | Sn calc. 26.9%, found 26,4% |
| | S calc. 7.3%, found 7.2%. |

EXAMPLE XV:

potassium S-triphenyl tin-ω-mercaptoheptanoate
$Ph_3Sn—S—CH_2(CH_2)—_4CH_2—COO.K$ The synthesis is carried under the conditions described in Example XII.

| Batch: | 36.7 parts of triphenyl tin hydroxide |
| --- | --- |
| | 16.2 parts of ω-mercaptoheptanoic acid |
| | 100 parts of toluene |
| | 6.2 parts of potassium hydroxide |
| | 50 parts of methanol |
| Yield: | 54 parts (98% of theory); wax-like consistency |
| | Sn calc. 21,6%, found 21,1% |
| | S calc. 5.8%, found 5.8%. |

EXAMPLE XVI:

sodium S-tri-n-butyl tin-γ-mercaptopropanesulphonate
$(C_4H_9)_3Sn—S—CH_2—CH_2—CH_2—SO_3.Na$ A solution of 60 g of bis-(tri-n-butyl tin)-oxide in 100 parts of toluene is added dropwise to a solution of 39 parts of sodium γ-mercaptopropanesulphonate and 50 parts of water. While stirring under reflux the water is removed by circulation and the solvent is subsequently distilled off under reduced pressure.

| Yield: | 87 parts (93,1% of theory); colourless powder; m.p. 260° – 263°C. |
| --- | --- |
| | Sn calc. 25.4%, found 25.0% |
| | S calc. 13.7%, found 14.0%. |

EXAMPLE XVII:

sodium S-triphenyl tin-γ-mercaptopropanesulphonate
$Ph_3Sn—S—CH_2—CH_2—CH_2—SO_3.Na$ While stirring, 36.7 parts of triphenyl tin hydroxide, 19,5 parts of sodium γ-mercaptopropanesulphonate, and 300 parts of methanol are heated for 2 hours under reflux. The undissolved portion (7.5 parts) is filtered off and the filtrate is concentrated in vacuo.

Yield: 45 parts (85,4% of theory). The product is purified by dissolving it in chloroform and then precipitating it with diethyl ether; m.p. 283° – 285°C.
Sn calc, 22.5%, found 21,9%
S calc, 12.2%, found 12.1%.

EXAMPLE XVIII:

triethylammonium S-tri-n-butyl tin-thioglycolate
$(C_4H_9)_3Sn—S—CH_2—COOH.N(—CH_2CH_2OH)_3$ To a solution of 46 parts of thioglycolic acid, 74,6 parts of triethanolamine and 100 parts of toluene are added 59,6 parts of bis-(tri-n-butyl tin)-oxide and the water of reaction is quantitatively removed by circulation while stirring. The solvent is subsequently distilled off in vacuo and the residue us recrystallised from acetonitrile.

Yield: 76,4 parts (72% of theory); colourless crystals; m.p. 64° – 67°C.

Sn calc. 22,4%, found 22,3%.

EXAMPLE XIX:

triethanolammonium S-tri-n-butyl tin-β-mercaptopropionate (C₄H₉)₃Sn—S—CH₂—CH₂—COOH.N(—CH₂—CH₂—OH)₃

The synthesis is carred out under the conditions described in Example XVIII.

| Batch: | 53 parts of β-mercaptopropionic acid |
| --- | --- |
| | 74 parts of triethanolamine |
| | 149 parts of bis-(tri-n-butyl tin)-oxide |
| | 150 parts of toluene |
| Yield: | 266 parts (98% of theory); yellow viscous liquid; |
| | $n_D^{20}$: 1.5182 |
| | Sn calc. 21,8%, found 21,5%. |

EXAMPLE XX:

triethanolamoonium S-triphenyl tin-thioglycolate

Ph₃Sn—S—CH₂COOH.N(—CH₂—CH₂—OH)₃

36,7 parts of triphenyl tin hydroxide are added to a solution of 9,2 parts of thioglycolic acid, 14,9 parts of triethanolamine, and 100 parts of tetrahydrofuran and the batch is stirred for 1 hour under reflux. The reaction mixture is subsequently cooled to 0°C and the precipitated product is filtered with suction and dried.

| Yield: 41,4 | parts (84% of theory); colourless crystals; |
| --- | --- |
| | m.p. 116° – 118°C. |
| | Sn calc. 20,1%, found 20,2 % |
| | SH calc. 5,6%, found 5,4%. |

EXAMPLE XXI:

S-tri-n-butyl tin-thioglycolic acid diethanolamide (C₄H₉)₃Sn—S—CH₂—CO.N(—CH₂—CH₂—OH)₂

While stirring, 39,5 parts of tri-n-butyl tin-thioglycolic acid methyl ester, 12,5 parts of diethanolamine, and 0,5 part of ammonium carbonate are heated in vacuo until no more methanol is distilled off.

| Yield: 46,7 | parts (96% of theory); colourless liquid; |
| --- | --- |
| | $n_D^{20}$: 1.5252 |
| | SH calc. 6.8%, found 6,5% |
| | Sn calc. 24,4% found 24,1% |

EXAMPLE XXII:

β-(S-tri-n-butyl tin)-mercaptoethyl-diethylmethylammonium-methyl-sulphate

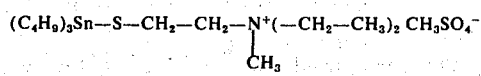
(C₄H₉)₃Sn—S—CH₂—CH₂—N⁺(—CH₂—CH₃)₂ CH₃SO₄⁻
                              |
                             CH₃

While stirring, 13,3 parts of diethylamino-ethane thiol, 100 parts of toluene, and 26,8 parts of bis-(tri-n-butyl tin)-oxide are heated under reflux until the water of reaction has been quantitatively removed by circulation. The solvent is subsequently distilled off in vacuo and the residue is treated with 100 parts of methanol and 12,6 parts of dimethyl sulphate. The batch is then heated under reflux for 20 minutes while stirring, then cooled and the solvent is distilled off under reduced pressure.

Yield: 48 parts (97% of theory); soap-like consistency.
Sn calc. 21,7%, found 20,9%.

EXAMPLE XXIII:

β-(S-triphenyl tin)-mercaptoethyl-diesthylmethylammonium-methyl-sulphate

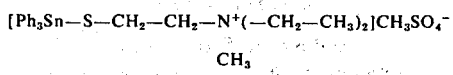
[Ph₃Sn—S—CH₂—CH₂—N⁺(—CH₂—CH₃)₂]CH₃SO₄⁻
                              |
                             CH₃

The synthesis is carried out under the conditions described in Example XXII.

| Batch: | 13,3 parts of diethylamino-ethane thiol |
| --- | --- |
| | 33.0 parts of triphenyl tin hydroxide |
| | 100 parts of toluene |
| | 100 parts of methanol |
| | 12.6 parts of dimethyl sulphate. |
| Yield: | 50 parts (97% of theory); yellow resin. |
| | Sn calc. 20,75%, found 20,5%. |

EXAMPLE XXIV:

S-tri-vinyl tin-thioglycolic acid-polyethylene glycol ester

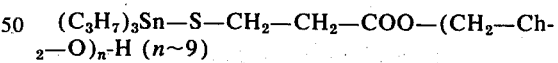
(CH₂=CH)₃Sn—S—CH₂—COO—(CH₂—CH₂—O)ₙ—H
(n~4,5)

The synthesis is carried out under the conditions described in Example I.

| Batch: | 20,0 parts of polyethylene glycol (MG~200) |
| --- | --- |
| | 9,2 parts of thioglycolic acid |
| | 21,7 parts of tri-vinyl-tin hydroxide |
| | 100 parts of toluene |
| Yield: | 46 parts (97,5% of theory); colourless liquid. |
| | Sn calc. 25,1%, found 25,0%. |

EXAMPLE XXV:

S-tri-n-propyl tin-β-mercaptopropionic acidpolyethylene glycol ester (C₃H₇)₃Sn—S—CH₂—CH₂—COO—(CH₂—CH₂—O)ₙ-H (n~9)

The synthesis is carried out under the conditions described in Example I.

| Batch: | 40,0 parts of polyethylene glycol (MG~400) |
| --- | --- |
| | 10,6 parts of β-mercaptopropionic acid |
| | 25.6 parts of bis-(tripropyl tin)-oxide |
| | 100 parts of toluene |
| Yield: | 71 parts (97% of theory); yellowish liquid; |
| | $n_D^{20}$: 1.4946 |
| | Sn calc. 16,15%, found 16,0%. |

EXAMPLE XXVI:

S-tri-n-pentyl tin-β-mercaptopropionic acidpolyethylene glycol ester

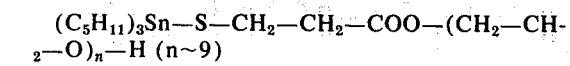
(C₅H₁₁)₃Sn—S—CH₂—CH₂—COO—(CH₂—CH₂—O)ₙ—H (n~9)

The synthesis is carried out under the conditions described in Example I.

| Batch: | 80,0 parts of polyethylene glycol (MG~400) |
|---|---|
| | 21,2 parts of β-mercaptopropionic acid |
| | 68,0 parts of bis-(tri-n-pentyl tin)-oxide |
| | 100,0 parts of toluene |
| Yield: | 159 parts (97% of theory): yellow liquid; |
| | $n_D^{20}$: 1.4895 |
| | Sn calc. 14,5%, found 14,4% |

EXAMPLE XXVII:

potassium S-tri-methyl tin-γ-mercapto-propanesulphonate $(CH_3)_3Sn-S-CH_2-CH_2-CH_2-SO_3 \cdot K$ The synthesis is carried out under the conditions described in Example XVI.

| Batch: | 19,4 parts of potassium γ-mercaptopropanesulphonate |
|---|---|
| | 50,0 parts of water |
| | 18,0 parts of tri-methyl tin hydroxide |
| | 100,0 parts of toluene |
| Yield: | 34 parts (95% of theory); colourless powder; |
| | m.p. > 250°C. |
| | Sn calc. 33,2%, found 32,9%. |

EXAMPLE XXVIII:

magnesium S-tri-methyl tin-β-mercaptopropionate
$[(CH_3)_3Sn.S-CH_2-CH_2-COO]_2 \cdot Mg$ The synthesis is carried out under the conditions described in Example XII.

| Batch: | 21,2 parts of β-mercaptopropionic acid |
|---|---|
| | 36,1 parts of tri-methyl tin hydroxide |
| | 100,0 parts of toluene |
| | 8,1 parts of magnesium oxide |
| | 50,0 parts of methanol. |
| Yield: | 52 parts (98,5% of theory); white powder; |
| | m.p.> 240°C. |
| | Sn calc. 22,5%, found 22,0% |
| | Mg calc. 4,6%, found 5,0%. |

EXAMPLE XXIX:

S-tri-cyclohexyl tin-β-mercaptopropionic acid-polyethylene glycol ester $Cy_3Sn-S-CH_2-CH_2-COO-(CH_2-CH_2-O)_n-H$ (n~9)

The synthesis is carried out under the conditions described in Example I.

| Batch: | 40,0 parts of polyethylene glycol (MG~400) |
|---|---|
| | 10,6 parts of β-mercaptopropionic acid |
| | 38,5 parts of tricyclohexyl tin hydroxide |
| | 100,0 parts of toluene |
| Yield: | 84 parts (98% of theory); yellowish liquid; |
| | Sn calc. 13,88%, found 13,6% |
| | S calc. 3,75%, found 3,8%. |

EXAMPLE XXX:

S-dimethylphenyl tin-β-mercaptopropionic acidpolyethylene glycol ester

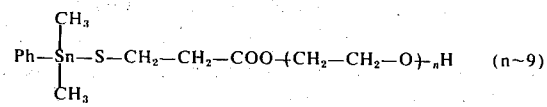

To a solution of 30,6 parts of dimethylphenyl tin bromide and 50 parts of methanol are added 5,4 parts of sodium methylate and the batch is stirred for 10 minutes at 30°C. The reaction mixture is subsequently treated with 48.8 parts of β-mercaptopropionic acid polyethylene glycol ester and 50 parts of i-propanol. The clear solution is concentrated in a rotary evaporator, and the residue is taken up with chloroform and purified neutral on silica gel (hydrated with 5% water). Subsequently the solvent is stripped off from the eluate.

| Yield: 63,5 | parts (87% of theory); yellowish liquid; |
|---|---|
| | $n_D^{20}$: 1.5326 |
| | Sn calc. 16,64%, found 16,9% |
| | S calc. 4,50%, found 4,3%. |

EXAMPLE XXXI:

S-dimethylcyclohexyl tin β-mercaptopropionic acid-polyethylene glycol ester

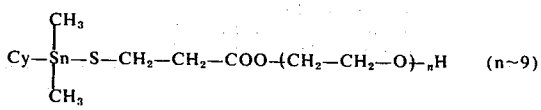

The synthesis is carried out under the conditions described in Example XXX.

| Batch: | 31,2 parts of dimethylcyclohexyl tin bromide |
|---|---|
| | 5,4 parts of sodium methylate |
| | 48,8 parts of β-mercaptopropionic acid polyethylene glycol ester |
| | 50,0 parts of methanol |
| | 50,0 parts of i-propanol |
| Yield: | 69,9 parts (97% of theory); yellowish liquid; |
| | Sn calc. 16,51%, found 16,2% |
| | S calc. 4,46%, found 4,5%. |

EXAMPLE XXXII:

S-dimethyl-n-octyl tin-β-mercaptopropionic acid-polyethylene glycol ester

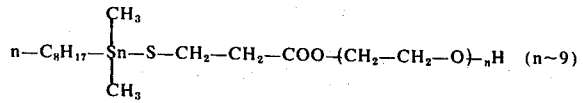

The synthesis is carried out under the conditions described in Example XXX.

| Batch: | 34,2 parts of dimethyl-n-octyl tin-bromide |
|---|---|
| | 5,4 parts of sodium methylate |
| | 48,8 parts of β-mercaptopropionic acid polyethylene glycol ester |

| | | |
|---|---|---|
| | 50,0 | parts of methanol |
| | 50,0 | parts of i-propanol |
| Yield: | 61,3 | parts (90% of theory); yellowish liquid; $n_D^{20}$: 1.4940 |
| | | Sn calc. 15,85%, found 15,9% |
| | | S calc. 4,28%, found 4,1%. |

EXAMPLE XXXIII:

sodium S-dimethyl-n-octyl tin-γ-mercapto-propanesulphonate

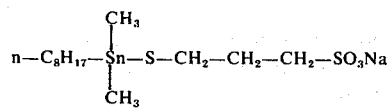

A solution of 51,3 parts of dimethyl-n-octyl tin bromide in 150 parts of methanol is treated with 8,1 parts of sodium methylate. The reaction mixture is stirred for 10 minutes at 30°C and subsequently 26,7 parts of sodium γ-mercaptopropanesulphonate dissolved in 40 parts of water are added dropwise. The clear solution is treated with chloroform and purified neutral on silica gel. The eluate is concentrated in a rotary evaporator and the residual solvent is distilled off in an oil pump.

| | | |
|---|---|---|
| Yield: | 63 | parts (96% of theory); semisolid mass; Sn calc. 27,03%, found 26,2%. |

EXAMPLE XXXIV:

S-dimethyl-n-butyl tin-β-mercaptopropionic acid polyethylene glycol ester

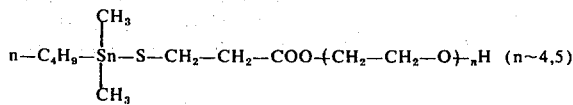

The synthesis is carried out under the conditions described in Example XXX.

| | | |
|---|---|---|
| Batch: | 42,8 | parts of dimethyl-n-butyl tin bromide |
| | 8,1 | parts of sodium methylate |
| | 43,2 | parts of β-mercaptopropionic acid polyethylene glycol ester |
| | 75,0 | parts of methanol |
| | 75,0 | parts of i-propanol |
| Yield: | 69 | parts (93% of theory); colourless liquid; Sn calc. 24,08%, found 23,6% S calc. 6,50%, found 6,3%. |

EXAMPLE XXXV:

β-(S-dimethyl-n-dodecyl)-mercaptoethyl-diethylmethylammonium-methylsulphate

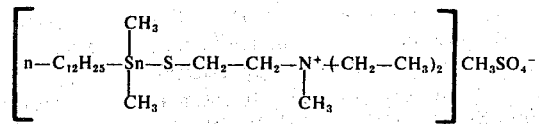

The synthesis is carried out under the conditions described in Example XXII.

| | | |
|---|---|---|
| Batch: | 13,3 | parts of diethylamino-ethane diol |
| | 33,5 | parts of dimethyl-n-dodecylhydroxide |
| | 100,0 | parts of toluene |
| | 12,6 | parts of dimethyl sulphate |
| | 100.0 | parts of methanol |
| Yield: | 57 | parts (99% of theory); soap-like consistency. |
| | | Sn calc. 20,59%, found 19,9% |
| | | S calc. 11,12%, found 11,3%. |

We claim:

1. A triorganotin compound of the general formula I

wherein $R_1$, $R_2$ and $R_3$ each independently represents a linear or branched aliphatic group with 1 to 16 carbon atoms, which can be saturated or singly olefinically unsaturated, a cyclopentyl, cyclohexyl or phenyl group, the sum of the carbon atoms of the substituents $R_1$, $R_2$ and $R_3$ being at most 18, and A represents a strongly hydrophilic residue selected from the group consisting of a. a polyethylene oxide of the formula
—$(CH_2CH_2O)_n$—H
with 2 to 15 ethylene oxide units ($n$ is 2 to 15), b. a carboxylate or sulphonate of the general formula II

wherein Q represents hydrogen or hydroxyl, p is a whole number from 1 to 6, X is —$CO_2$— or —$SO_3$—, or where p is 0, X is the succinic acid radical, the p-benzenesulphonic acid radical or the o-benzoic acid radical and Y represents an once or twic charged cation with $g=1$ in the first case and $l = ½$ in the second case, c. a carboxylic acid ester or a carboxylic acid amide of formula II, wherein Q and p have the same meaning given hereinbefore, X is —CO—, q is 1 and Y represents for the ester a polyethylene oxide radical of the formula —O—$(CH_2CH_2O)_n$-H in which $n$ is 2 to 15, a polyhydroxyalkyl radical of the formula

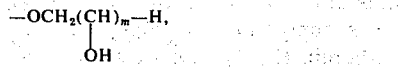

in which $m$ is 2 to 6, or radicals of pentaerythritol, dipentaerythritol or trimethylolpropane, and for the amide the radical of primary or secondary amine- polyethylene oxide adducts of the formulae

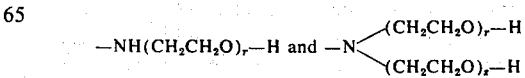

wherein $r$ is in the first case 1 to 15 and $r$ and $s$ in the second case are numbers which are the same or different, the sum of $r$ and $s$ being 2 to 15, and d. an ammonium salt of formula II wherein Q and p have the meanings given hereinbefore, X represents a radical of the formulae

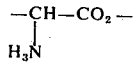

or $-NZ_3^+$ wherein Z represents lower alkyl groups, which are the same or different, polyethylene oxide radicals with 2 to 6 ethylene oxide units, β-hydroxyethyl and/or hydrogen, or where $p$ is 0, X represents

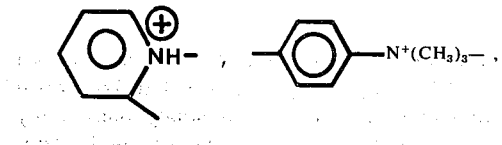

or

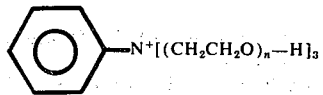

wherein $n$ is 1 to 6, and Y represents a monovalent or divalent negative counterion, wherein in the first case $q=1$ and in the second case $q=½$.

2. A compound according to claim 1, of formula I, wherein $R_1$, $R_2$ and $R_3$ each independently represents alkyl with 1 to 4 carbon atoms, vinyl, 3-butenyl, cyclohexyl or phenyl.

3. A compound according to claim 1, of the formula I, wherein the substituents $R_1$ and $R_2$ are the same.

4. A compound according to claim 1, of the formula I, wherein the substituents $R_1$, $R_2$, and $R_3$ are the same.

5. A compound according to claim 1, of the formula I, wherein $R_1$ and $R_2$ represent methyl, and $R_3$ represents butyl, octyl, cyclohexyl, or phenyl.

6. A compound according to claim 1, of the formula I, wherein $R_1$, $R_2$, and $R_3$ are the same and represent n-butyl, cyclohexyl, or phenyl.

7. A compound according to claim 1, of the formula I, wherein -S-A represents the radical of a salt of an aliphatic mercapto-carboxylic acid with at most 5 carbon atoms, and which contain sodium, potassium, or the triethanolammonium group as cation.

8. A compound according to claim 1, of the formula I, wherein -S-A represents a carboxylic acid ester radical of the formula $-S-(CH_2)_p-COO-(CH_2-CH_2-O)_n-H$, wherein $p$ is 1 to 4 and $n$ is 2 to 15.

9. A compound according to claim 1, of the formula I, wherein -S-A represents the radical of the salt of a mercaptoalkanesulphonic acid with at most 6 carbon atoms.

10. A compound according to claim 1, of the formula I, wherein the polyethyleneoxide has 8 to 11 ethylene oxide units.

11. A compound according to claim 1, of the formula I, wherein -S-A represents the 2-mercaptopropionate or mercaptoacetate radical and which contain sodium, potassium or the triethanolammonium group as cation.

12. A compound according to claim 1, of the formula I, wherein -S-A represents the 3-mercaptopropanesulphonate radical.

13. A compound according to claim 1, of the formula I, wherein for the carboxylic acid ester or amide, Q represents in formula II hydrogen and $p$ is 1 or 2.

14. A compound according to claim 1, of the formula I, wherein n in the $-O-(CH_2-CH_2-O)_n-H-$ radical is 8 to 11.

15. A compound according to claim 1, of the formula I, wherein the sum of $r$ and $s$ in the amine-polyethylene adduct is 2.

16. A compound according to claim 1, of the foumula I, wherein Z in the $NZ_3^+$-group of the ammonium salt is the β-hydroxyethyl radical.

17. A compound according to claim 1, of the formula n-butyl$_3$Sn—S—CH$_2$—CH$_2$—CO—O $\leftarrow$ CH$_2$—CH$_2$—O $_n$—H, wherein $n$ has a value of about 9.

18. A compound according to claim 1, of the formula

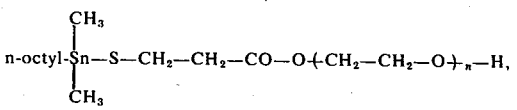

wherein $n$ has a value of about 9.

19. A compound according to claim 1, of the formula n-butyl$_3$—Sn—S—CH$_2$—CO$_2$. HN(CH$_2$—CH$_2$—OH)$_3$.

20. A compound according to claim 1, of the formula

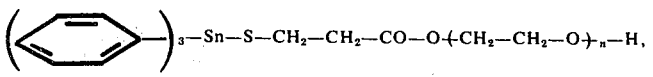

wherein $n$ has a value of about 15.

21. A compound according to claim 1, of the formula

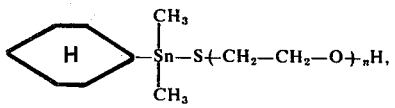

wherein n has a value of about 8.

22. A compound according to claim 1, of the formula $(CH_3)_3Sn-S-CH_2CH_2COOCH_2C(CH_2OH)_2CH_2CH_3$.

23. A compound according to claim 1, of the formula n-butyl$_3$Sn—S—CH$_2$CON(CH$_2$CH$_2$OH)$_2$ 24. A compound according to claim 1, of the formula n-butyl$_3$Sn—S—CH$_2$CH$_2$CH$_2$SO$_3$.Na 25. A compound according to claim 1, of the formula
n-butyl₃Sn—S—(CH₂CH₂O)ₙH,
wherein *n* has a value of about 14.

26. A compound according to claim 1, of the formula

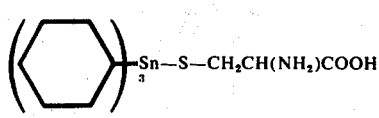

27. A compound according to claim 1, of the formula

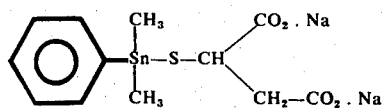

28. A compound according to claim 1, of the formula

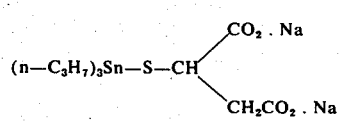

29. A compound according to claim 1, of the formula

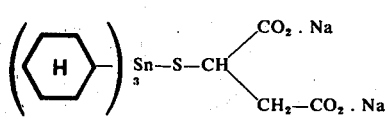

30. A compound according to claim 1, of the formula

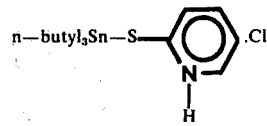

31. A compound according to claim 1, of the formula

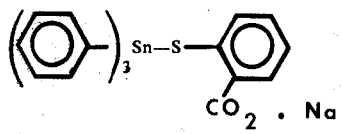

32. A compound according to claim 1, of the formula 33. a compound according to claim 1, of the formula
i-propyl₃Sn—S—CH₂—CH₂—CH₂—CH₂N(CH₃)(C₂H₅)₂. SO₄CH₃

34. A compound according to claim 1, of the formula

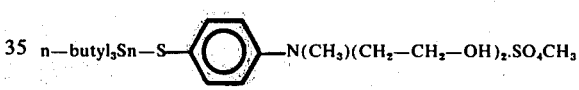

* * * * *